(12) United States Patent
Tittgen

(10) Patent No.: US 6,800,752 B2
(45) Date of Patent: Oct. 5, 2004

(54) CHROMATOGRAPHY MATERIAL AND A METHOD USING THE SAME

(75) Inventor: Jochen Tittgen, Bünde (DE)

(73) Assignee: Dr. Tittgen Biotechnologie (DE)

( * ) Notice: Subject to any disclaimer, the term of this patent is extended or adjusted under 35 U.S.C. 154(b) by 26 days.

(21) Appl. No.: 10/168,467

(22) PCT Filed: Dec. 20, 2000

(86) PCT No.: PCT/EP00/13034

§ 371 (c)(1),
(2), (4) Date: Aug. 7, 2002

(87) PCT Pub. No.: WO01/46686

PCT Pub. Date: Jun. 28, 2001

(65) Prior Publication Data

US 2003/0040621 A1 Feb. 27, 2003

(30) Foreign Application Priority Data

Dec. 23, 1999 (DE) .......................................... 199 62 577

(51) Int. Cl.$^7$ ............................................ C07H 21/04
(52) U.S. Cl. .................................... 536/25.4; 435/306.1
(58) Field of Search ....................... 536/25.4; 435/306.1

(56) References Cited

U.S. PATENT DOCUMENTS

4,780,369 A * 10/1988 Schnabel et al. ............ 428/398
5,451,370 A * 9/1995 Jones .......................... 422/56

FOREIGN PATENT DOCUMENTS

| DE | 36 09 021 A1 | 9/1986 |
| DE | 43 34 359 A1 | 4/1995 |
| EP | 000443734 A1 * | 8/1991 |
| WO | WO 83/03363 | 10/1983 |
| WO | WO 95/22053 | 8/1995 |

OTHER PUBLICATIONS

Bart et al. "Continuous Separation of Carbohydrates by the Use of Annular Chromatography", 1998, Wissenschaftliche Kurznitteilungen, pp. 142–144.

* cited by examiner

Primary Examiner—James Ketter
(74) Attorney, Agent, or Firm—Piper Rudnick LLP

(57) ABSTRACT

A chromatography material for separation of nucleic acid mixtures, having a carrier and ion exchanger functions applied to it is described, whereby the carrier comprises a fibrous material. In addition, a method that is performed with the chromatography material according to this invention is also described.

18 Claims, 4 Drawing Sheets

CHROMATOGRAPHY MATERIAL AND A METHOD USING THE SAME

RELATED APPLICATION

This application is a 371 of PCT/EP00/13034 filed Dec. 20, 2000 which claims priority from German Patent Appln. No. 199 62 577.8 filed Dec. 23, 1999.

FIELD OF THE INVENTION

The present invention relates to a chromatography material for separation of nucleic acid mixtures and a method of separating nucleic acid mixtures using this chromatography material.

BACKGROUND

The use of chromatography and the chromatography materials used in this process have become indispensable in such fields as biochemistry, medicine, pharmacy and genetic engineering. With the help of chromatography materials, biomolecules such as nucleic acids and proteins are rapidly and systematically separated and isolated. In molecular biology, it is often necessary to isolate certain nucleic acids, which are present in this mixture in concentrations of less than 0.1%, from a naturally occurring mixture of more than a hundred different components. The requirements of a chromatographic method and the chromatography material used in the method therefore include, first, quantitative isolation of the nucleic acids, and secondly, quantitative separation of impurities to thereby purify the nucleic acid as a molecular species until it is homogeneous for subsequent analysis.

In the known chromatography methods, inorganic granular chromatography materials having defined particle and pore sizes are used, their surface having been modified with a silanizing reagent to produce a stationary phase. The reaction with a reagent forming an anion or cation exchanger then leads to the finished chromatography material.

For example, International Patent WO 91/05606 describes a carrier material for chromatography which is suitable for separation of various species of nucleic acids. Suitable carriers include silica gel, aluminum oxide, titanium dioxide, porous glass or resins. The carrier material should have a particle size of 3 to 500 $\mu$m with a pore size of approximately 10 to 1000 nm and a specific surface area of 5 to 800 $m^2/g$. The surface of this granular support is silanized with alkoxysilanes. Thus, in addition, a chromatographic carrier material is described, which is based on silica gel and having anion exchanger groups that are obtained by reacting the alkoxysilane with a secondary hydroxylamine.

Thus, according to European Patent 0 104 210, silica gel materials have a particle size of 3 to 100 $\mu$m, a void size of 10 to 1000 nm and a specific surface area of 5 to 800 $m^2/g$ are described. These materials are then treated at the surface with a silanizing agent and used with ion exchanger functions in chromatography for separation of nucleic acids.

Finally, European Patent 0744025 discloses a chromatography material in which a carrier of silica gel is reacted with a silanizing reagent, whereby carrier materials having a pore diameter of 4 to 6 nm are selected. The particle size of the carrier is 1 to 500 $\mu$m.

In chromatographic separation of nucleic acid mixtures using conventional granular chromatography materials, it has been found that it is very time-consuming to perform such separations. For example, if a certain column was used with a modified silica gel as the carrier for chromatography, it would be expected that an adsorption time of the nucleic acids on the carrier of at least 20 minutes under gravity flow conditions would have to be accepted.

The chromatography materials known in the past have also had a defined porosity, because according to the prevailing opinion only a porous support, i.e., one with an enlarged surface area, would guarantee sufficient loading with ion exchanger. However, this porosity has the disadvantage that the quality of nucleic acid separation is not optimum. This is attributed to the fact that other substances present in the mixture during separation, e.g., RNA and proteins, diffuse into the pores and thus have a negative effect on the separation process.

Thus, would be advantageous to make available a chromatography material that could perform a separation of nucleic acid mixtures within the shortest possible period of time, while at the same time achieving an excellent resolution of the nucleic acid mixtures and thus an excellent purity of the nucleic acids isolated.

It would also be advantageous to make available a method with which a nucleic acid mixture can be separated with the highest possible resolution and purity of the individual components in the shortest possible amount of time.

SUMMARY OF THE INVENTION

The present invention relates to a chromatography material for separating nucleic acid mixtures, having a carrier and ion exchanger functions applied to it, wherein the carrier is a fibrous material.

This invention relates to a method of separating nucleic acid mixtures with the chromatography material according to this invention, where the chromatographic separation of the nucleic acids is performed by the action of a force.

The subclaims concern preferred embodiments of the method according to this invention.

This invention also concerns a kit for separating nucleic acid mixtures which contains a chromatography material according to the present invention. The kit includes the chromatography material according to this invention in the desired arrangement together with corresponding buffers for performing the chromatographic separation of nucleic acid mixtures using the chromatographic material.

BRIEF DESCRIPTION OF THE DRAWINGS

This invention is explained on the basis of the figures, which show.

DETAILED DESCRIPTION

Figure 1:
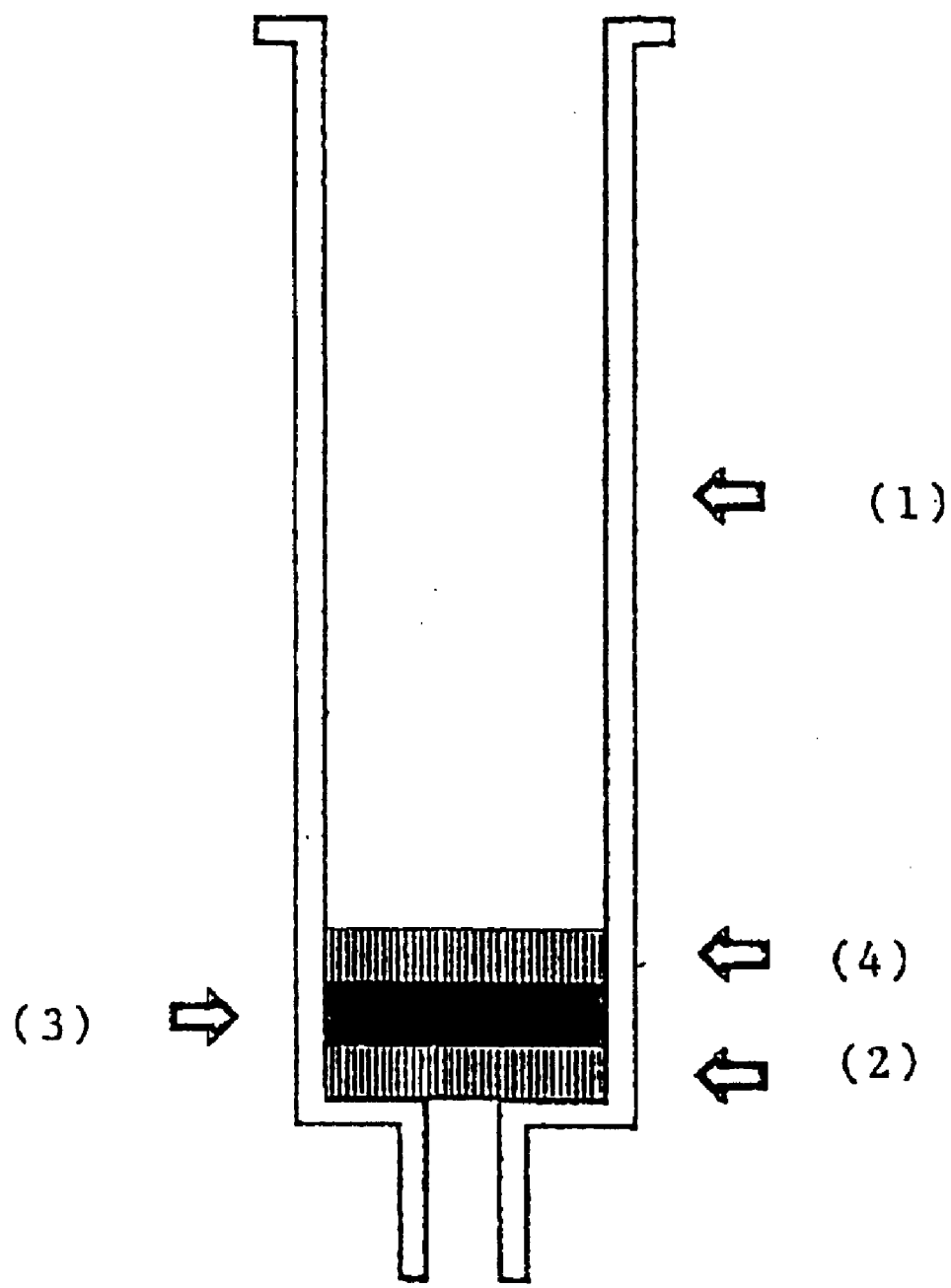
FIG. 1 an example of a column using the chromatographic material according to this invention.

It has surprisingly been found according to this invention that a significantly improved separation capacity can be achieved if the carrier of the chromatography material includes a fibrous material whose surface area is not enlarged or is only insignificantly enlarged. Contrary to the prevailing opinion, the chromatography material according to this invention may be loaded with a corresponding amount of functional ion exchanger groups to guarantee an excellent separation capacity.

The specific surface area of the carrier is in the range of 0.05 to 50 m$^2$/g, preferably in the range of 1 to 10 m$^2$/g, in particular 1 to 5 m$^2$/g.

Fibrous materials suitable for modification of their surface area with ion exchanger functions may be used as the carrier. A suitable material for the carrier would be, for example, micro-fibers, whereby micro-glass fibers are preferred. Such materials have a pore-free surface.

In a preferred embodiment, the fibrous material may be subjected to an acid or base treatment before being used as a carrier.

The fibrous carrier may be in the form of a mass which may be used directly for chromatography. However, it is also possible to process the mass further for separation into suitable forms.

It has been found that for many applications the chromatography material according to this invention advantageously includes a carrier which is in the form of a membrane. For a suitable capacity of the chromatography material, it is preferable for the membrane to have a thickness of at least 0.05 mm, regardless of the total surface area.

In a preferred embodiment of the chromatography material according to this invention, the membrane is in the form of a single layer. However, it is also possible for the membrane to be in multiple layers, depending on the desired separation capacity.

The carrier of the chromatography material according to this invention is reacted with a silanizing reagent. For example, the silanizing reagent may be the one described in International Patent WO 91/05606. Likewise, anion exchanger groups or cation exchanger groups may be applied to the stationary phase by known methods. An example of this is described in International Patent WO 91/05606.

The chromatography material according to this invention has the advantage that when using this material, it is possible to perform a separation of nucleic acid mixtures within an extremely short period of time. The reason for this is that there is a sufficient retention time for separation of the nucleic acids even in the presence of strong forces, e.g., a vacuum acting on the chromatography material according to this invention, which has a higher material density than traditional chromatography materials. Because of the high material density that can be achieved, separation of nucleic acids may be performed with a very small bed volume. The washing and elution volumes are also low accordingly.

The chromatography material according to this invention is used to separate nucleic acid mixtures with an extremely high accuracy and purity of the fractions to be obtained. This is manifested in particular by comparison with the traditional granular chromatography materials. To this end, the nucleic acid mixtures were allowed to run on an agarose gel on the chromatography material according to this invention and two traditional chromatography materials both before and after separation into RNA and DNA.

Figure 2:
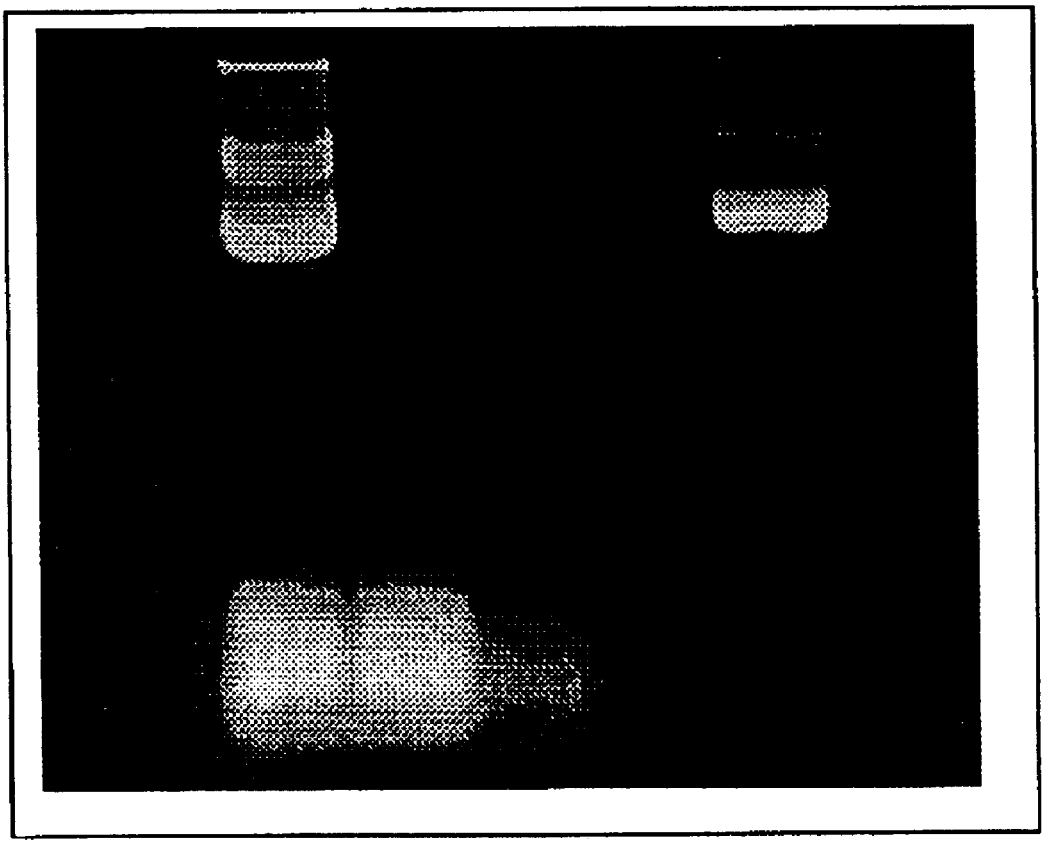
FIG. 2 separation of nucleic acid mixture components on an agarose gel using the chromatography material according to this invention.

FIG. 2 shows the separation of the nucleic acid mixture components using the chromatography material according to this invention. The individual lanes show the runs through the column:

Lane L: cleared lysate before separation
Lane D: column run
Lane W 1: first washing
Lane W 2: second washing
Lane E: elution The same experiment was conducted with traditional chromatography materials. To do so, reference is made to FIGS. 3 and 4. The same column runs were applied in the tracks.

FIG. 2 shows that in the eluate in lane E, the RNA is completely separated from the plasmid DNA. In addition, it can be seen clearly that the individual runs before elution do not entail any loss of DNA.

Figure 3:
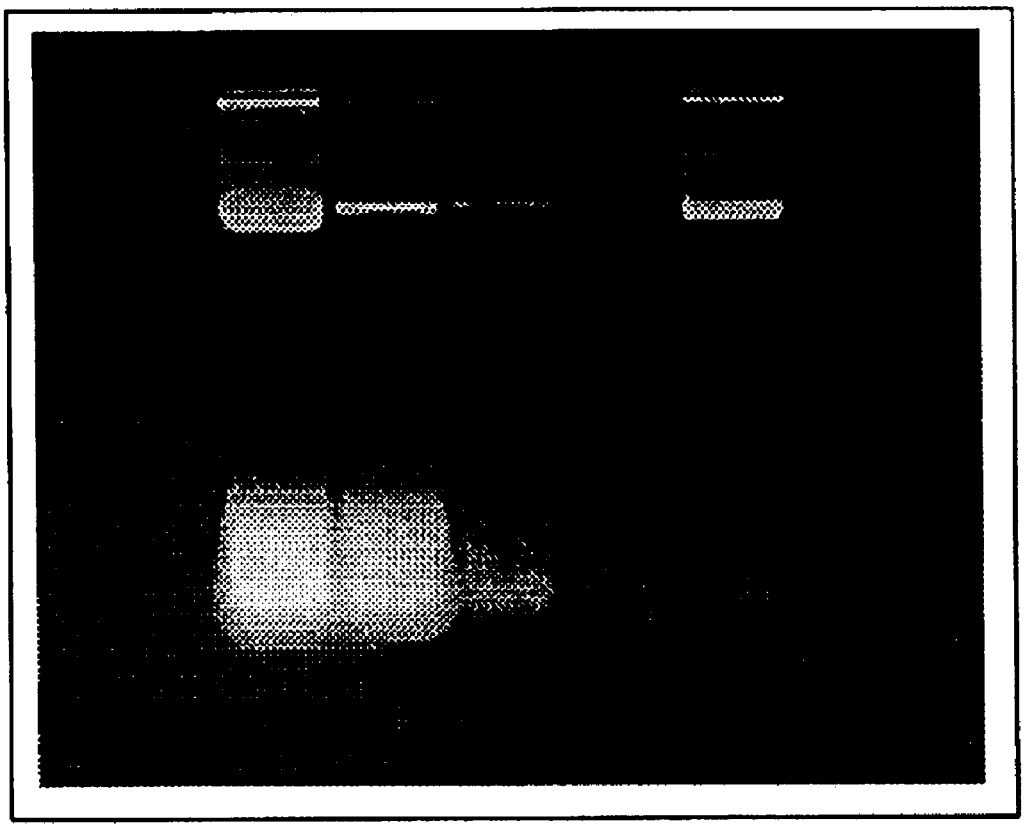
FIG. 3 separation of nucleic acid mixture components on an agarose gel using a state-of-the-art chromatography material, and FIG. 4 separation of nucleic acid mixture components on an agarose gel using a state-of-the-art chromatography material.
Figure 4:
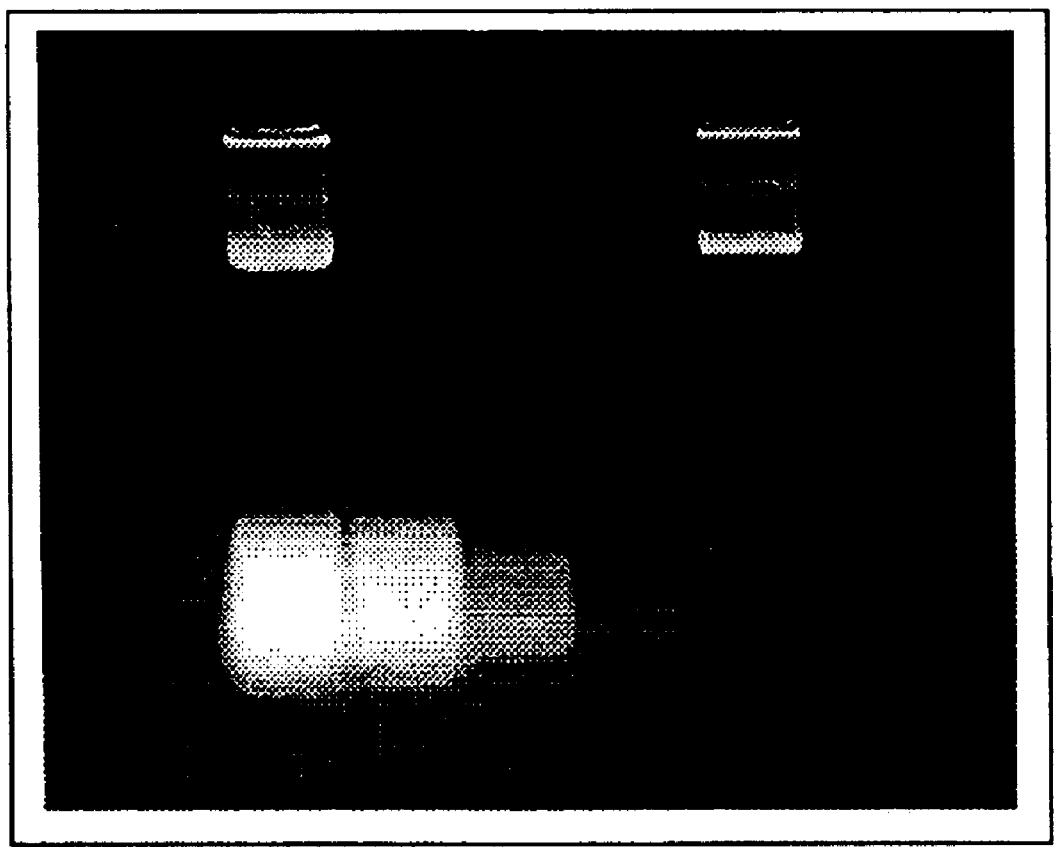

FIGS. 3 and 4 show the separation of nucleic acid mixture components using traditional granular chromatography materials. In the purification in FIG. 3 in particular, a great loss of DNA is indicated in lane E. Furthermore, there is a poor reduction in concentration of RNA, which is shown in lane W 2, where significant quantities of RNA continue to be present in the second washing run.

A poor reduction in concentration is also obtained when using another traditional chromatography material in FIG. 4. Lane W 2 shows considerable RNA still present in the second washing.

Another advantage in comparison with traditional granular chromatography materials is that no particles of the chromatography material (fines) are present in the eluate E. This leads to a considerable improvement in the quality of the nucleic acids thus obtained.

The method according to this invention for separating nucleic acid mixtures using the chromatography material according to this invention is characterized in that it is performed under the influence of a force.

In a preferred embodiment, the method is performed by applying a vacuum.

For example, after application of the nucleic acid mixture sample to the chromatography material according to this invention, a vacuum is applied, inducing separation within a approximately twenty seconds. This is in gross contrast with the traditional silica gel columns which require a separation time of at least twenty minutes with gravity flow when using a bed volume at least ten times greater.

The chromatography element according to this invention may be used in virtually all chromatographic processes. These include column chromatography, separation in spin columns and spin cups or separation in batch processes, where the chromatography material is in suspension or is adsorbed on reaction vessels, microtiter plates, pipette tips, stirring rods or test strips.

In chromatographic separation in spin cups, the centrifugal force is utilized in that the specimen which is placed in spin cups is separated chromatographically in a centrifuge.

Any nucleic acid mixture can be separated very effectively by using the chromatography material according to this invention. It is thus possible to isolate DNA with an extremely high purity from mixtures containing only very small quantities of DNA in addition to large quantities of RNA. Furthermore, it is possible to completely avoid using toxic substances such as phenol, chloroform or ethidium bromide. In addition, the separation may be performed entirely without the use of RNAse.

FIG. 1 shows an example of a column equipped with the chromatography material according to this invention. A bottom frit (2) having a thickness of 1 mm sealed with the outlet is provided in a conventional commercial plastic column (1) having an outlet that tapers toward the bottom for applying a vacuum. The chromatography material (3) according to this invention in the form of a micro-glass fiber membrane with a thickness of 2 mm is applied to this. In conclusion, a top frit (4) 1 mm thick is provided on top of that.

Similar arrangements are used in all other chromatography methods, e.g., in spin cups and on microtiter plates (96-well plates).

The method according to this invention for separating nucleic acid mixtures using the chromatography material according to this invention is carried out in a simple step gradient by washing the arrangement loaded with the nucleic acid mixture and then eluting the desired nucleic acid with a suitable buffered salt solution. Most of the RNA is separated during binding of the DNA to the chromatography material according to this invention, and the remaining RNA is washed out during the washing operation. Thus, a treatment with RNAse is not necessary.

If the chromatographic separation is carried in a column or a microtiter plate, for example, then separation is performed on the arrangement of components by applying a vacuum within an extremely short period of time, i.e., in approximately twenty seconds. Likewise, separation with an excellent efficiency is achieved in spin cups which are placed in a centrifuge, and then the separation is performed by centrifugal force within a very short period of time, such as approximately twenty seconds.

The chromatography material according to this invention may be brought on the market in various ways. For example, it is possible to offer the chromatography material according to this invention in the desired arrangement as a kit together with the equipment required for the chromatography, e.g., buffers. Other commercial forms are of course also included.

This invention is illustrated now on the basis of the following examples, although without being restricted to them.

EXAMPLES

Example 1: Culturing the Bacterial Cultures

E. coli cultures are cultured according to conventional microbiological practice for the plasmid preparations. On day 1, an isolation smear is prepared from a deep-frozen stock culture on a selective medium (e.g., LB agar with ampicillin as the antibiotic). After incubation overnight at 37° C., a well grown single colony is inoculated on 50 to 300 ml liquid medium (e.g., LB) to which the corresponding antibiotic has been added on day 2. After another overnight incubation at 37° C. on a shaker with good ventilation (200 to 300 rpm), even larger volumes of culture are optionally stocked up or the culture that has been grown is harvested directly. In the case of stocking up, the corresponding amount of fresh liquid medium mixed with the respective antibiotic is inoculated with the culture of the preceding day in the amount of 1% of its volume and incubated on the shaker at 200 to 300 rpm for another overnight incubation at 37° C.

For a mini-preparation, 1 to 3 ml culture with high-copy plasmid or 5 to 20 ml culture with low-copy plasmid is used. In the case of midi- or maxi-preparations, larger amounts are used accordingly.

Example 2: Isolation of DNA from Bacteria

The amount of bacterial culture indicated in Example 1 for a mini-preparation is centrifuged for three minutes at 13,000×g in a suitable centrifuge vessel, and the supernatant medium is discarded completely. Any medium running back from the edge of the centrifuge vessel is removed with a pipette and also discarded.

The pelletized bacteria are completely re-suspended by vortexing in 0.4 ml buffer at 50 mM Tris-HCl (pH 8.0)/10 mM EDTA/100 μg/ml RNAse. There must not be any visible cell clumps or cell aggregates.

The suspended cells are lysed by adding 0.4 ml buffer of 200 mM NaOH/0.1% (w/v) SDS. The suspended cells are mixed with the lysis buffer by inverting several times until forming a homogeneous phase. This phase has a very high viscosity due to the genomic bacterial DNA emerged. It is incubated for a maximum of five minutes at room temperature.

The lysis mixture is neutralized by adding 0.4 ml buffer of 3.1–3.4 M potassium acetate (pH 5.5 with acetic acid). After adding the buffer, the mixture is blended by inverting repeatedly until obtaining a homogeneous phase. This phase then has a low viscosity again. There must not be any viscous residues of cell lysate.

The precipitate of bacterial proteins and cell debris precipitated in neutralization is centrifuged by centrifuging for 10 minutes at ≧13,000×g at room temperature, and the clear supernatant ("cleared lysate") is pipetted out.

Example 3: Producing a Column Using the Chromatography Material According to this Invention 5 g pore-free glass fibers having a specific surface area of 5 m$^2$/g is mixed with 60 g 3-glycidoxypropyltrimethoxysilane and 0.13 ml triethylamine in 750 ml dry xylene. The reaction mixture is degassed by applying a vacuum three times and then aerating with nitrogen and next heating for four hours at 130° C. in the absence of air and moisture. The mixture is filtered and washed with xylene and tetrahydrofuran. The modified glass fiber is dried in vacuo at 50° C.

The product is then mixed with 750 ml and 42 g diethylamine and heated for 18 hours at reflux. The product is washed with dioxane and methanol and dried at 70° C. in vacuo. The modified glass fiber mass having an anion exchanger function is then processed further to form an anion exchanger membrane. The glass fiber mass is slurried in acetone and rolled into the proper form or cast and then dried. A membrane is cut to conform to the column diameter and inserted into the arrangement according to FIG. 1.

Example 4: Separation of the Bacterial DNA

The column according to example 3 is connected to a suitable vacuum chamber (e.g., VacMan, Promega). The ion exchanger membrane is equilibrated with 2 mL buffer of 100 mM NaAc/HAc (pH 5.0)/600 mM NaCl. To do so, the buffer is pipetted into the column and pulled completely through the membrane by applying a water jet vacuum. The vacuum pump remains turned on until no liquid is being detectably sucked away from the membrane. Then the vacuum is switched off.

The column is loaded with the cleared lysate from Example 2, which is drawn completely through the membrane by applying the water jet vacuum. The vacuum pump remains in operation until it is apparent that no more liquid is being removed from the membrane. Then the vacuum is turned off.

To remove non specifically bound components, the column is washed with 2.5 ml buffer of 100 mM NaAc/HAc (pH 5.0)/600 mM NaCl. To do so, the buffer is pipetted into the column and drawn completely through the membrane by applying a water jet vacuum. The vacuum pump remains turned on until it is apparent that no more liquid is being removed from the matrix. Then the vacuum is turned off.

This washing step is repeated once in the case of the mini- and midi-preparation.

The column is detached from the vacuum chamber and the plasma DNA bound to the membrane is eluted directly into a suitable vessel by adding 0.8 ml buffer of 100 mM Tris-HCl (pH 8.5)/1250 mM NaCl. To do so, the buffer is pipetted into the column and forced manually through the membrane with the help of a suitable stamp. To do so, the elution buffer should be forced through in a rapid sequence of drops, but by no means as a stream. Individual droplets must still be clearly discernible with the naked eye.

The eluates are mixed with 0.7 vol isopropanol (room temperature) and mixed well. The plasma DNA precipitated in this way is centrifuged for 30 minutes at $\geq 13{,}000 \times g$ and 4° C. and the supernatant is discarded. The pelletized DNA is washed once with 80% ethanol, centrifuged again, then dried (either by leaving to stand at room temperature or in vacuo) and the dried DNA is finally dissolved in a suitable amount of TE buffer or water for ten minutes at 37° C.

The dissolved plasmid DNA is measured by spectrophotometry and analyzed on an agarose gel.

FIG. 2 shows the separation of the components of the mixture on a 1% agarose gel using a TAE buffer pH 8.3. The following components were applied in the individual lanes:

Lane L: cleared lysate before separation
Lane D: column run
Lane W1: first washing
Lane W2: second washing
Lane E: elution The lanes L, D and W1 show clearly that RNA is still present in the preparation. However, complete separation of the nucleic acid mixture components is clearly apparent in the eluate in lane E which shows only plasmid DNA without any RNA contamination.

Example 5: Separation of Bacterial DNA

The same bacterial DNA as in Example 2 was applied to a column from Macherey-Nagel (Nucleobond Kits) containing a traditional chromatography material and separated according to the manufacturer's instructions. The results are shown in FIG. 3.

Example 6: Separation of Bacterial DNA

A traditional chromatography material from the company Qiagen (Qiagen Plasmid Kits) was used to separate the bacteria of Example 2. The manufacturer's instructions were also followed here. The results are shown in FIG. 4.

What is claimed is:

1. A chromatography material for separating nucleic acid mixtures comprising a carrier and ion exchanger functional groups applied to the carrier, wherein the carrier is composed of pore free micro-glass fibers.

2. The chromatography material according to claim 1, wherein the carrier has a specific surface area of 0.05 to 50 $m^2/g$.

3. The chromatography material according to claim 1, wherein the micro-glass fibers are in the form of a mass.

4. The chromatography material according to claim 3, wherein the mass is a membrane.

5. The chromatography material according to claim 4 wehre in the membrane has a thickness of at least 0.05 mm.

6. The chromatography material according to claim 5, wherein the membrane is formed in a single layer.

7. The chromatography material according to claim 6, wherein the membrane is formed of multiple layers.

8. The chromatography material according to claim 1, wherein the carrier is reacted with a silanizing reagent.

9. A chromatography material for separating nucleic acid mixtures comprising a carrier and ion exchanger functional groups applied to the carrier, wherein the carrier is composed of micro-glass fibers and the carrier is reacted with a silanizing reagent, and wherein the ion exchanger functional groups are anion exchanger groups linked by the silanizing reagent.

10. A chromatography material for separating nucleic acid mixtures comprising a carrier and ion exchanger functional groups applied to the carrier, wherein the carrier is composed of micro-glass fibers and the carrier is reacted with a silanizing reagent, and wherein the ion exchanger functional groups are cation exchanger groups linked by the silanizing reagent.

11. A method of separating nucleic acid mixtures using a chromatography material that comprises a carrier a chromatography material for separating nucleic acid mixtures comprising a carrier and ion exchanger functional groups applied to the carrier, wherein the carrier is composed of micro-glass fibers, comprising applying force to the nucleic acids to perform chromatographic separation.

12. The method according to claim 11, wherein the force is a vacuum.

13. The method according to claim 11, wherein the chromatographic separation is performed in a column or on microtiter plates.

14. The method according to claim 13, wherein the separation is performed by centrifugal force.

15. The method according to claim 14, wherein the chromatographic separation is performed in spin cups in a centrifuge.

16. The method according to claim 11, wherein the chromatographic separation is performed in a step gradient.

17. The method according to claim 11, wherein no RNAse is used.

18. A kit for separating nucleic acid mixtures containing chromatography material according to claim 1.

* * * * *

UNITED STATES PATENT AND TRADEMARK OFFICE
CERTIFICATE OF CORRECTION

PATENT NO. : 6,800,752 B2
DATED : October 5, 2004
INVENTOR(S) : Tiggen et al.

It is certified that error appears in the above-identified patent and that said Letters Patent is hereby corrected as shown below:

Column 8,
Line 9, please change "wehre in" to -- wherein --.

Signed and Sealed this

Eighth Day of February, 2005

JON W. DUDAS
*Director of the United States Patent and Trademark Office*